United States Patent [19]

Takatsu et al.

[11] Patent Number: 4,657,750
[45] Date of Patent: Apr. 14, 1987

[54] PROCESS FOR THE PRODUCTION OF CRYSTALLINE SILICATE ISI-4 USING ETHYLENE GLYCOL

[75] Inventors: Kozo Takatsu, Sodegaura; Noboru Kawata, Ichihara, both of Japan

[73] Assignee: Research Association for Petroleum Alternatives Development, Tokyo, Japan

[21] Appl. No.: 713,086

[22] Filed: Mar. 18, 1985

Related U.S. Application Data

[62] Division of Ser. No. 512,996, Jul. 12, 1983, abandoned.

[30] Foreign Application Priority Data

Jul. 30, 1982 [JP] Japan ................. 57-132143

[51] Int. Cl.[4] ............................................. C01B 33/28
[52] U.S. Cl. ..................... 423/329; 423/326; 423/328; 423/330; 423/331; 423/332; 423/333; 502/60; 502/62; 502/71; 502/77
[58] Field of Search ................. 423/328–330; 502/60, 62, 71, 77

[56] References Cited

U.S. PATENT DOCUMENTS

| | | | |
|---|---|---|---|
| 4,076,842 | 2/1978 | Plank et al. | 423/328 |
| 4,086,186 | 4/1978 | Rubin et al. | 423/328 |
| 4,242,233 | 12/1980 | Ball et al. | 423/329 X |
| 4,346,021 | 8/1982 | Ball et al. | 423/328 X |
| 4,377,502 | 3/1983 | Klotz | 502/77 |
| 4,431,621 | 2/1984 | Taramasso et al. | 423/328 |
| 4,474,741 | 10/1984 | Hoelderich et al. | 423/329 |
| 4,526,879 | 7/1985 | Dwyer et al. | 423/329 |
| 4,578,259 | 3/1986 | Morimoto et al. | 423/329 |

FOREIGN PATENT DOCUMENTS

| | | | |
|---|---|---|---|
| 0042225 | 12/1981 | European Pat. Off. | 423/329 |
| 2071632 | 9/1981 | United Kingdom | 423/328 |

Primary Examiner—John Doll
Assistant Examiner—Jackson Leeds
Attorney, Agent, or Firm—Frishauf, Holtz, Goodman & Woodward

[57] ABSTRACT

Crystalline silicates and processes for the production thereof are described. These crystalline silicates are of new crystalline structure, which, as determined after calcination in the air at 550° C., have a composition represented by the general formula (I): $pM_{2/n}O.Al_2O_3.qSiO_2$ (the symbols are as defined in the appended claims) and give a X-ray diffraction pattern as shown in Table 2. They are superior in heat resistance and acid resistance, and can be used as catalysts for the conversion of various organic compounds, absorbents, or as catalysts for various reactions. They are produced by reacting an aqueous mixture comprising (a) a silica source, (b) an alumina source, (c) an alkali metal and/or alkaline earth metal source, and (d) ethylene glycol or (e) monoethanolamine at a temperature of 100° to 300° C. till the desired crystalline silicates are formed. Although ethylene glycol and monoethanolamine do not remain in the crystalline silicates, they play important roles in the formation of the desired crystalline structure in the course of the production thereof.

8 Claims, 1 Drawing Figure

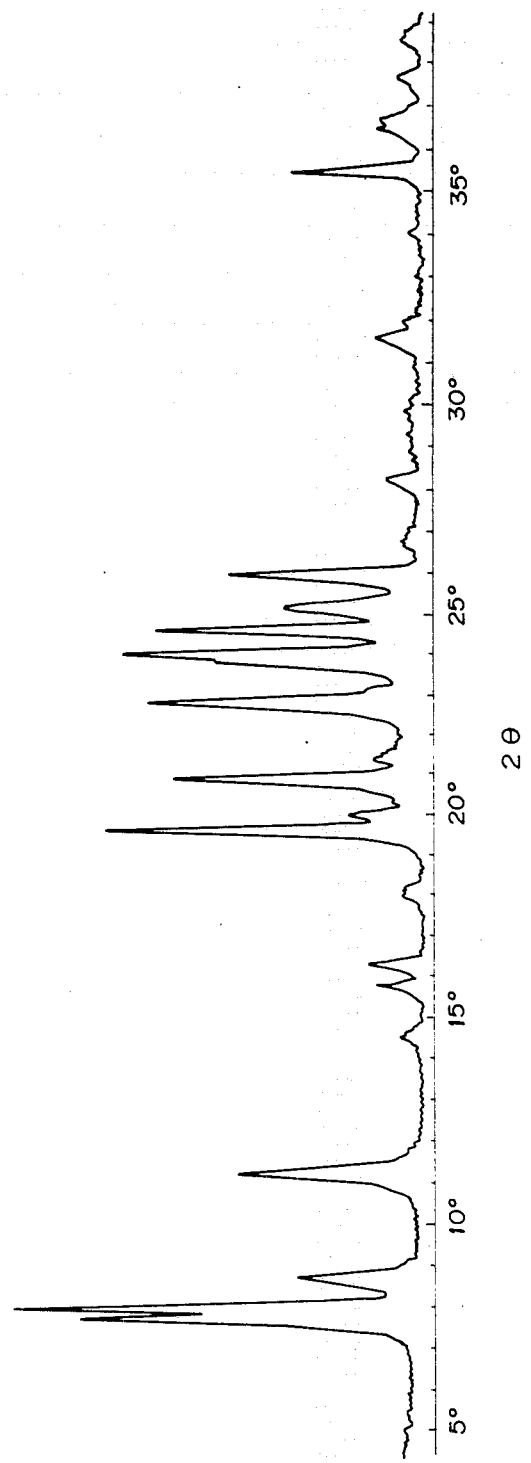

PROCESS FOR THE PRODUCTION OF CRYSTALLINE SILICATE ISI-4 USING ETHYLENE GLYCOL

This application is a division of application Ser. No. 512,996 filed July 12, 1983, now abandoned.

BACKGROUND OF THE INVENTION

The present invention relates to crystalline silicates of novel structure and a process for the production of said crystalline silicates. More particularly, the present invention relates to crystalline silicates having a novel structure which can be effectively used as catalysts for various chemical reactions, and also to a process for efficiently producing said crystalline silicates. These crystalline silicates are called herein crystalline silicates (ISI-4).

A number of crystalline silicates, natural or synthetic, have heretofore been known, and various processes for the production thereof have been proposed. In general, these crystalline silicates are produced by preparing an aqueous mixture consisting of a silica source, an alumina source, and an alkali metal source and, thereafter, subjecting the aqueous mixture to a hydrothermal reaction.

Recently, a method has been developed to produce crystalline silicate zeolites with a specific structure by adding organic compounds exemplified by tetrapropylammonium bromide to the aqueous mixture. For example, Japanese Patent Application Laid-Open No. 134517/81 describes that ZSM-5 zeolite is produced by adding diols to the aqueous mixture. Also, Japanese Patent Application Laid-Open No. 107499/79 describes that crystalline aluminosilicate zeolites with specific structure are produced by adding monoethanolamine. Although the structure is not shown, examination of the examples of Japanese Patent Application Laid-Open No. 17920/81 in which nearly the same conditions as in Japanese Patent Application Laid-Open No. 107499/79 are employed reveals that the crystalline aluminosilicate zeolites are similar to ZSM-5 zeolite.

As a result of extensive investigations to develop silicates with a novel composition and a novel crystalline structure, it has been found that, although organic compounds such as monoethanolamine are added in small amounts in relation to the silica source or alumina source in conventional methods, if ethylene glycol or monoethanolamine of the organic compounds is added in such a large amount as to be a solvent, crystalline silicates with a novel structure are obtained.

SUMMARY OF THE INVENTION

The present invention provides:

(1) a crystalline silicate named as "ISI-4" having a composition, as determined after calcination in the air at 550° C., represented by the general formula (I):

$$pM_{2/n} O \cdot Al_2O_3 \cdot qSiO_2 \qquad (I)$$

(wherein M represents at least one element selected from hydrogen, alkali metals and alkaline earth metals, n represents the valence of M, and p and q each represents a molar ratio and is chosen within the ranges of $0.3 \leq p \leq 3.0$ and $q \geq 10$) and giving a principal X-ray diffraction pattern, also as determined after calcination in the air at 550° C., as shown in Table 1 as described hereinafter;

(2) a process for producing the crystalline silicate as defined in (1) above, which comprises reacting an aqueous mixture comprising (a) a silica source, (b) an alumina source, (c) an alkali metal and/or alkaline earth metal source, and (d) ethylene glycol in the following molar ratios:

silica/alumina ≧ 10/1,
ethylene glycol/water = 0.05/1 to 10/1,
ethylene glycol/silica = 2/1 to 100/1,
hydroxyl ion/silica = 0.01/1 to 0.5/1 (excluding hydroxyl ions resulting from organic bases) at a temperature of 100° to 300° C. till the desired crystalline silicate is formed; and (3) a process for producing the crystalline silicate as defined in (1) above, which comprises reacting an aqueous mixture comprising (a) a silica source, (b) an alumina source, (c) an alkali metal and/or alkaline earth metal source, and (e) monoethanolamine in the following molar ratios:

silica/alumina ≧ 10/1,
monoethanolamine/water = 0.05/1 to 10/1,
monoethanolamine/silica = 2/1 to 100/1,
hydroxyl ion/silica = 0.01/1 to 0.5/1 (excluding hydroxyl ions resulting from organic bases) at a temperature of 100° to 300° C. till the desired crystalline silicate is formed.

TABLE 1

| Lattice Spacing d (Å) | Relative Intensity |
|---|---|
| 11.31 ± 0.2 | strong |
| 10.92 ± 0.2 | very strong |
| 7.83 ± 0.2 | medium |
| 4.51 ± 0.15 | very strong |
| 4.24 ± 0.1 | strong |
| 3.89 ± 0.1 | strong |
| 3.73 ± 0.1 | medium |
| 3.69 ± 0.1 | very strong |
| 3.61 ± 0.1 | very strong |
| 3.53 ± 0.07 | medium |
| 3.43 ± 0.07 | strong |
| 2.52 ± 0.05 | medium |

Irradiation: Cu—K$_\alpha$
Wavelength: 1.5418Å

BRIEF DESCRIPTION OF THE DRAWING

The FIGURE shows an X-ray diffraction pattern of the crystalline silicate (ISI-4) obtained in Example 1 as described hereinafter. In the FIGURE, θ means the angle of the incidence.

DETAILED DESCRIPTION OF THE INVENTION

In accordance with the present invention, (a) a silica source, (b) an alumina source, (c) an alkali metal and/or alkaline earth metal source, and (d) ethylene glycol or (e) monoethanolamine are added to water to prepare an aqueous mixture, and the aqueous mixture is then reacted till the desired crystalline silicate is formed.

The silica source (a) as used herein is not critical, and silica powder, silicic acid, colloidal silica, dissolved silica, etc. can be used. Examples of such dissolved silicas include water glass silicate and alkali metal silicate, containing 1 to 5 moles of $SiO_2$ per mole of $Na_2O$ or $K_2O$.

As the alumina source (b), various compounds can be used, including aluminum sulfate, sodium aluminate, colloidal alumina, and alumina.

The ratio of silica to alumina in the aqueous mixture can be determined appropriately. The molar ratio of silica ($SiO_2$) to alumina ($Al_2O_3$) is preferably at least 10:1, and the optimum molar ratio is from 40:1 to 1,000:1.

As the alkali metal and/or alkaline earth metal source (c), various compounds can be used. For example, sodium hydroxide, potassium hydroxide, etc. can be used as the alkali metal source. Sodium silicate and sodium aluminate serve also as the silica source and the alumina source, respectively. A particularly preferred alkali metal is sodium. As the alkaline earth metal source, calcium nitrate, calcium chloride, etc. can be used.

The molar ratio of alkali metal and/or alkaline earth metal to silica in the aqueous mixture is not critical and can be determined appropriately depending on various conditions. It is usually from 0.05:1 to 6:1 and particularly preferably from 0.1:1 to 3:1.

Ethylene glycol (d) does not remain in the ultimate crystalline silicate, but plays an important role in forming the desired crystalline structure in the course of the production thereof. It is preferred that ethylene glycol be used in relatively large amounts. For example, the molar ratio of ethylene glycol to water is from 0.05:1 to 10:1 and particularly preferably from 0.1:1 to 5:1, and the molar ratio of ethylene glycol to silica is from 2:1 to 100:1 and particularly preferably from 4:1 to 10:1. In the present invention, monoethanolamine (e) can be used in place of ethylene glycol (d). Monoethanolamine (e) plays the same role as ethylene glycol (d). Also with regard to the amount of monoethanolamine being added, it is preferred to be used in relatively large amounts. For example, the molar ratio of monoethanolamine to water is from 0.05:1 to 10:1 and particularly preferably from 0.1:1 to 5:1, and the molar ratio of monoethanolamine to silica is from 2:1 to 100:1 and particularly preferably from 4:1 to 10:1.

In the aqueous mixture prepared by adding the foregoing components (a), (b), (c), and (d) or (e) to water, the molar ratio of hydroxyl ion to silica should be adjusted to from 0.01:1 to 0.5:1. In this case, the moles of hydroxyl ions are calculated excluding those ions resulting from the addition of organic bases such as monoethanolamine.

The aqueous mixture is reacted by heating under the condition, e.g., temperatures and perids of time, that are required for forming the desired crystalline silicate (ISI-4). In more detail, it is sufficient for the aqueous mixture to be heated at a temperature of from 100° to 300° C., preferably from 120° to 200° C. for a period of time of from 5 hours to 10 days, preferably from 10 hours to 5 days. There is no special limitation to the pressure at which the reaction is performed. Usually the reaction is performed at autogenous pressure. The reaction is usually performed while stirring and, if necessary, may be performed in an inert gas atmosphere. Although the pH of the reaction system is not critical, it is preferred to be adjusted to at least 7.5, with the range of from 7.5 to 12.0 being particularly preferred.

It is required for the reaction of crystallization to be performed always in the presence of ethylene glycol or monoethanolamine. Unless this requirement is satisfied, the desired crystalline silicate (ISI-4) cannot be obtained. In this reaction, there is no special limitation to the order in which the components are mixed. In a preferred embodiment, an aqueous aluminum salt solution, an aqueous silicate solution, and an aqueous alkali metal salt and/or alkaline earth metal salt solution are added dropwise concurrently to water and mixed and, thereafter, ethylene glycol or monoethanolamine is added to the mixture.

After the crystallization reaction is completed, the resulting reaction mass is washed with water and dried at about 120° C. and then is calcined in the air at 550° C. for 6 hours, whereby there can be obtained the crystalline silicate (ISI-4) having a composition represented by the general formula (I) and giving a principal X-ray diffraction pattern as shown in Table 1.

Relative intensities of lattice spacings other than the principal lattice spacings shown in Table 1 are not critical in the crystalline silicate (ISI-4) of the invention. Preferred, however, are those crystalline silicates giving an X-ray diffraction pattern as shown in Table 2 below.

TABLE 2

| Lattice Spacing d (Å) | Relative Intensity |
|---|---|
| 11.31 ± 0.2 | strong |
| 10.92 ± 0.2 | very strong |
| 10.03 ± 0.2 | weak |
| 7.83 ± 0.2 | medium |
| 6.08 ± 0.15 | weak |
| 5.61 ± 0.15 | weak |
| 5.24 ± 0.15 | weak |
| 4.90 ± 0.15 | weak |
| 4.51 ± 0.15 | very strong |
| 4.42 ± 0.1 | weak |
| 4.24 ± 0.1 | strong |
| 4.14 ± 0.1 | weak |
| 3.89 ± 0.1 | strong |
| 3.73 ± 0.1 | medium |
| 3.69 ± 0.1 | very strong |
| 3.61 ± 0.1 | very strong |
| 3.53 ± 0.07 | medium |
| 3.43 ± 0.07 | strong |
| 3.32 ± 0.07 | weak |
| 3.16 ± 0.07 | weak |
| 2.97 ± 0.07 | weak |
| 2.83 ± 0.05 | weak |
| 2.52 ± 0.05 | medium |

Irradiation: Cu—$K_\alpha$
Wavelength: 1.5418Å

The relative intensity was determined as shown below with the intensity at the lattice spacing of 10.92±0.2 Å as 100%.

| Very strong: | 70 to 100% |
| Strong: | 50 to 70% |
| Medium: | 30 to 50% |
| Weak: | 0 to 30% |

The crystalline silicate (ISI-4) of the present invention is a silicate having a new crystalline structure and shows superior heat resistance and acid resistance and, therefore, can be used, for example, as a catalyst for use in the reaction of conversion of various organic compounds, an absorbent, and a catalyst for various reactions. When the crystalline silicate (ISI-4) is used as a catalyst, for example, hydrocarbons can be produced from oxygen-containing compounds obtained from coal, biomass, etc. by a simplified process and moreover in a high conversion over a long period of time. Also, when the crystalline silicate (ISI-4) is used as a catalyst, liquid hydrocarbons having large amount of aromatic components can be efficiently produced from hydrocarbons having small amount of aromatic components.

Oxygen-containing compounds which can be used in the production of hydrocarbons include compounds containing from 1 to 4 carbon atoms, such as alcohols, ethers, aldehydes, and carboxylic acids. In more detail, methanol, ethanol, propanol, butanol, dimethyl ether, diethyl ether, acetaldehyde, propylaldehyde, acetic acid, propionic acid, etc. can be used. Of these compounds, methanol is particularly preferred. Production of hydrocarbons from such oxygen-containing compounds can be carried out by contacting the oxygen-containing compounds with the crystalline silicate (ISI-4) catalyst. The production reaction is carried out at atmospheric pressure or under pressure. As for other conditions of the reaction, the temperature is from 250° to 600° C. and preferably from 300° to 500° C., and the weight hourly space velocity (WHSV) is from 0.1 to 50 per hour and preferably from 0.5 to 10 per hour. This reaction enables to produce olefins of high practical value, particularly ethylene, propylene and butene, from oxygen-containing compounds obtained from feedstocks other than oil, such as coal and biomass, in a high selectivity. In addition, xylene can be produced, in which the p-xylene content is very high. Moreover, hydrocarbons such as butane can be produced efficiently.

In efficiently producing the foregoing liquid hydrocarbons having large amount of aromatic components, as described above, hydrocarbons having small amount of aromatic components are used as feedstocks. There is no special limitation to the type of hydrocarbon used as feedstocks. Moreover, the aromatic component content in the hydrocarbons is not critical, but those hydrocarbons having an aromatic component content of 15% by weight or less are usually employed. Examples of such hydrocarbon feedstocks are naphtha fractions such as a light naphtha and a heavy naphtha. Particularly suitable are fractions having a number of carbon atoms of at least 4 and a boiling point of 200° C. or lower, especially those fractions having a number of carbon atoms of at least 4 and a boiling point of 140° C. or lower. In addition, olefins or paraffins containing from 2 to 4 carbon atoms can be used alone or in combination with each other and moreover in mixture with the foregoing naphtha fraction. In particular, it is preferred to use a mixture of the above-described naphtha fraction and olefin containing from 2 to 4 carbon atoms. In this case, when the weight ratio of olefin to naphtha fraction is adjusted to 0.05:1 to 19:1, with the weight ratio of from 0.18:1 to 5.7:1 being particularly preferred, there are produced liquid hydrocarbons having large amount of aromatic components as compared with the case in which they are used separately; that is, the so-called synergistic effect can be obtained. This reaction is usually carried out at a pressure of from atmospheric pressure to 50 kilograms per square centimeter by gauge, preferably from atmospheric pressure to 20 kilograms per square centimeter by gauge, a temperature of from 200° to 550° C., preferably from 300° to 500° C., and a weight hourly space velocity (WHSV) of from 0.1 to 50 per hour, preferably from 0.5 to 10 per hour. In accordance with this reaction, liquid hydrocarbons having large amount of aromatic components and of very high practical value, such as a gasoline fraction, can be produced very efficiently from those hydrocarbons having small amount of aromatic components and low practical value. Light gases as by-product herein can be recycled and used as hydrocarbon feed-stocks.

Thus the crystalline silicate (ISI-4) of the invention can be used widely in oil refinery, production of gasoline, or in various chemical industries.

The present invention is described in greater detail by reference to the following examples.

EXAMPLE 1

Solution A consisting of 7.52 grams of aluminum sulfate (18 hydrates), 17.6 grams of sulfuric acid (97%) and 100 milliliters of water, and Solution B consisting of 211 grams of water glass ($SiO_2$: 29.0% by weight, $Na_2O$: 9.4% by weight, water: 61.6% by weight) and 46 milliliters of water were prepared. Solutions A and B were gradually added dropwise to 100 milliliters of water at the same time and mixed. Then, 6 grams of sulfuric acid (50%) was added, and the resulting mixture was adjusted to pH 9.5. In addition, 376 milliliters of ethylene glycol was added thereto and mixed. The thus-prepared aqueous mixture was then placed in a one-liter autoclave and reacted with stirring at 170° C. and autogenous pressure for 20 hours.

The reaction mixture was cooled and, thereafter, washed five times with 1.5 liters of water. It was then filtered, and the resulting solid was dried at 120° C. for 6 hours to obtain 55.0 grams of crystalline silicate. Then it was calcined in the air at 550° C. for 6 hours. Thus obtained crystalline silicate had a composition (expressed in a molar ratio) of $0.9Na_2O.Al_2O_3.74.0SiO_2$, and gave an X-ray diffraction pattern as shown in the FIGURE.

EXAMPLE 2

The procedure of Example 1 was repeated with the exception that monoethanolamine was used in place of ethylene glycol. The thus-obtained crystalline silicate had the same composition and X-ray diffraction pattern as in Example 1.

EXAMPLE 3

Solution A consisting of 1.85 grams of sodium aluminate, 7.2 grams of sodium hydroxide (95%) and 236 milliliter of water, and Solution B consisting of 200 grams of colloidal silica ($SiO_2$: 30% by weight, water: 70% by weight) were prepared. Solutions A and B were gradually added dropwise at the same time and mixed. The thus-prepared mixture was reacted, and then washed and dried in the same manner as in Example 1 to obtain 52.0 grams of crystalline silicate. The composition (expressed in a molar ratio) of the crystalline silicate was $0.8Na_2O.Al_2O_3.76.0SiO_2$.

APPLICATION EXAMPLE 1

The crystalline silicate (ISI-4) produced in Example 1 was subjected to an ion exchange reaction at room temperature for one day and night with 5 milliliters of 1 normal ammonium nitrate per gram of the crystalline silicate. The crystalline silicate was then washed with pure water and dried at 120° C. and, thereafter, calcined at 550° C. for 6 hours in the air to produce a H-type silicate. To this H-type was added an alumina sol in the amount (calculated as alumina) of 35% by weight, and the resulting mixture was extrusion-molded and calcined at 550° C. for 6 hours in the air to obtain a catalyst.

The thus-produced catalyst (2.5 grams) was placed in a flow type reactor, with which methanol was contacted for 4 hours under the conditions of atmospheric pressure, 370° C., and WHSV=2.0 per hour while passing it through the reactor. The results are shown in Table 3.

COMPARATIVE EXAMPLE 1

Crystalline aluminosilicate ZSM-34 (1.0 gram, produced by the procedure disclosed in Japanese Patent Application Laid-Open No. 58499/78) was charged to a flow type reactor, with which methanol was contacted for 5.5 hours under the conditions of atmospheric pressure, 371.1° C., and WHSV=3.0 per hour while passing it through the reactor. The results are shown in Table 3.

TABLE 3

|  | Application Example 1 | Comparative Example 1 |
|---|---|---|
| Conversion of Methanol (%) | 93.5 | 85.9 |
| Hydrocarbon Composition (wt %) |  |  |
| Methane | 1.8 | 2.3 |
| Ethane | 0.2 | 0 |
| Ethylene | 16.7 | 25.9 |
| Propane | 2.6 | 2.1 |
| Propylene | 17.6 | 17.6 |
| Butane | 15.3 | 1.9 |
| Butene | 13.7 | 5.4 |
| Hydrocarbons containing 5 or more carbon atoms ($C_5{}^+$) | 32.2 | 45.1 |
| Composition of Xylene* (wt %) |  |  |
| p-Xylene | 83.5 | — |
| m-Xylene | 10.8 | — |
| o-Xylene | 5.8 | — |

*The isomer composition of xylene contained in hydrocarbons containing 5 or more carbon atoms is shown. The xylene content of the hydrocarbons containing 5 or more carbon atoms was 11.9% by weight.

APPLICATION EXAMPLE 2

The same catalyst as used in Application Example 1 was charged to a flow type reactor, with which olefin-containing gas with the composition shown in Table 4 was contacted under the conditions of atmospheric pressure, 450° C., and WHSV=1.0 per hour while passing it through the reactor. The results are shown in Table 6.

APPLICATION EXAMPLE 3

The procedure of Application Example 2 was repeated with the exception that liquid hydrocarbon with the composition shown in Table 5 was used as a hydrocarbon feedstock in place of the olefin-containing gas. The results are shown in Table 6.

APPLICATION EXAMPLE 4

The procedure of Application Example 2 was repeated with the exception that a 30:70 (by weight) mixture of the olefin-containing gas of the composition shown in Table 4 and the liquid hydrocarbon of the composition shown in Table 5 was used as a hydrocarbon feedstock in place of the olefin-containing gas. The results are shown in Table 6.

APPLICATION EXAMPLE 5

The procedure of Application Example 2 was repeated with the exception that a 50:50 (by weight) mixture of the olefin-containing gas of the composition shown in Table 4 and the liquid hydrocarbon of the composition shown in Table 5 was used as a hydrocarbon feedstock in place of the olefin-containing gas. The results are shown in Table 6.

TABLE 4

| Component | Proportion (wt %) |
|---|---|
| Ethane | 0 |
| Ethylene | 0 |
| Propane | 0.2 |
| Propylene | 0.1 |
| iso-Butane | 38.0 |
| n-Butane | 6.7 |
| l-Butene | 14.7 |
| iso-Butene | 33.4 |
| trans-2-Butene |  |
| cis-2-Butene | 6.9 |
| $C_5{}^+$ | 0.1 |

TABLE 5

| Component | Proportion (wt %) |
|---|---|
| Butane | 2.9 |
| iso-Pentane | 16.3 |
| n-Pentane | 28.5 |
| n-Hexane | 16.5 |
| Other $C_6{}^+$ compounds | 35.8 |

TABLE 6

|  | Application Example 2 | Application Example 3 | Application Example 4 | Application Example 5 |
|---|---|---|---|---|
| Reaction Conditions |  |  |  |  |
| Pressure | atmospheric pressure | atmospheric pressure | atmospheric pressure | atmospheric pressure |
| Temperature (°C.) | 450 | 450 | 450 | 450 |
| WHSV (hr$^{-1}$) | 1.0 | 1.0 | 0.3 + 0.7*1 | 0.5 + 0.5*1 |
| Conversion of Butene (%) | 91.3 | — | 92.1 | 93.1 |
| Reaction Results |  |  |  |  |
| Methane (wt %) | 0.9 | 0.0 | 0.4 | 0.5 |
| Ethane + Ethylene (wt %) | 1.6 | 1.1 | 1.3 | 1.2 |
| $C_3$ (Propylene) (wt %) | 9.3 (2.9) | 18.5 (1.3) | 14.2 (1.1) | 14.6 (1.5) |
| $C_4$ (butene) (wt %) | 72.3 (4.8) | 49.5 (3.1) | 58.0 (4.3) | 60.8 (3.7) |
| $C_5{}^+$ (wt %) | 15.9 | 30.9 | 26.1 (26.4)*2 | 22.9 (23.5)*2 |
| Aromatic Fraction/$C_5{}^+$ (wt %) | 68.3 | 25.1 | 41.3 (32.9)*2 | 51.2 (39.6)*2 |

*1 The left-hand figure indicates the WHSV of the olefin-containing gas, and the right-hand figure indicates the WHSV of the liquid hydrocarbon.
*2 Expected values on basis of the results of Application Examples 2 and 3.

What is claimed is:

1. A process for producing a crystalline silicate, when determined after calcination in the air at 550° C., having a composition represented by the general formula (I), $$pM_{2/n}O \cdot Al_2O_3 \cdot qSiO_2 \qquad (I)$$

wherein M represents at least one element selected from hydrogen, alkali metals, and alkaline earth metals, n represents the valence of M, and p and q each represent a molar ratio and are chosen within the ranges of $0.3 \leq p \leq 3.0$, $q \geq 10$, and giving a principal X-ray diffraction pattern as shown in Table 1, below:

TABLE 1

| Lattice Spacing d (Å) | Relative Intensity |
|---|---|
| 11.31 ± 0.2 | strong |
| 10.92 ± 0.2 | very strong |
| 7.83 ± 0.2 | medium |
| 4.51 ± 0.15 | very strong |
| 4.24 ± 0.1 | strong |
| 3.89 ± 0.1 | strong |
| 3.73 ± 0.1 | medium |
| 3.69 ± 0.1 | very strong |
| 3.61 ± 0.1 | very strong |
| 3.53 ± 0.07 | medium |
| 3.43 ± 0.07 | strong |
| 2.52 ± 0.05 | medium | which process consists essentially of reacting an aqueous mixture consisting essentially of (a) a silica source, (b) an alumina source, (c) an alkali metal and/or alkaline earth metal source, and (d) ethylene glycol in the following molar ratios:

silica/alumina $\geq 10/1$,
ethylene glycol/water = 0.05/1 to 10/1,
ethylene glycol/silica = 5.5/1 to 10/1,
hydroxyl ion/silica = 0.01/1 to 0.5/1 excluding hydroxyl ions resulting from organic bases, at a temperature of 100° to 300° C. until the desired crystalline silicate is formed.

2. A process as claimed in claim 1, wherein the X-ray diffraction pattern is as shown in Table 2 below:

TABLE 2

| Lattice Spacing d (Å) | Relative Intensity |
|---|---|
| 11.31 ± 0.2 | strong |
| 10.92 ± 0.2 | very strong |
| 10.03 ± 0.2 | weak |
| 7.83 ± 0.2 | medium |
| 6.08 ± 0.15 | weak |
| 5.61 ± 0.15 | weak |
| 5.24 ± 0.15 | weak |
| 4.90 ± 0.15 | weak |
| 4.51 ± 0.15 | very strong |
| 4.42 ± 0.1 | weak |
| 4.24 ± 0.1 | strong |
| 4.14 ± 0.1 | weak |
| 3.89 ± 0.1 | strong |
| 3.73 ± 0.1 | medium |
| 3.69 ± 0.1 | very strong |
| 3.61 ± 0.1 | very strong |
| 3.53 ± 0.07 | medium |
| 3.43 ± 0.07 | strong |
| 3.32 ± 0.07 | weak |
| 3.16 ± 0.07 | weak |
| 2.97 ± 0.07 | weak |
| 2.83 ± 0.05 | weak |
| 2.52 ± 0.05 | medium |

Irradiation: Cu—K$_\alpha$
Wavelength: 1.5418Å

3. The process of claim 1 wherein M is sodium.
4. The process of claim 1 wherein M is potassium.
5. The process of claim 1 wherein M is calcium.
6. The process of claim 1 wherein said crystalline silicate has the formula $0.9Na_2O.Al_2O_3.74.0SiO_2$.
7. The process of claim 1 wherein said crystalline silicate has the formula $0.8Na_2O.Al_2O_3.76.0SiO_2$.
8. A process as claimed in claim 1, wherein said ethylene glycol/silica molar ratio is about 6.6–6.7/1.

* * * * *